United States Patent

Wilcox

[11] 4,169,721
[45] Oct. 2, 1979

[54] N-(ORTHO-SUBSTITUTED BENZYL)-DINITRO-TRIFLUOROMETHYL-ANILINES AS PLANT GROWTH REGULANTS

[75] Inventor: Merrill Wilcox, Gainesville, Fla.

[73] Assignee: Ciba-Geigy Corporation, Ardsley, N.Y.

[21] Appl. No.: 857,486

[22] Filed: Dec. 5, 1977

Related U.S. Application Data

[63] Continuation of Ser. No. 628,693, Nov. 5, 1975, abandoned, which is a continuation-in-part of Ser. No. 533,046, Dec. 16, 1974, abandoned.

[51] Int. Cl.$^2$ .............................................. A01N 9/20
[52] U.S. Cl. ........................................ 71/121; 71/78; 260/570.9
[58] Field of Search ....................... 71/121; 260/570.9

[56] References Cited

U.S. PATENT DOCUMENTS

| | | | |
|---|---|---|---|
| 3,227,758 | 1/1966 | Richter et al. | 260/570.9 |
| 3,406,024 | 10/1968 | Richter et al. | 260/570.9 X |
| 3,686,230 | 8/1972 | Maravetz | 71/121 |
| 3,880,643 | 4/1975 | Cooke et al. | 71/121 X |

FOREIGN PATENT DOCUMENTS 2108346  9/1971  Fed. Rep. of Germany ........ 260/570.9

*Primary Examiner*—Robert V. Hines
*Attorney, Agent, or Firm*—Frederick H. Rabin

[57] ABSTRACT

N-(ortho-substituted benzyl)-dinitro-trifluoromethylanilines of the formula

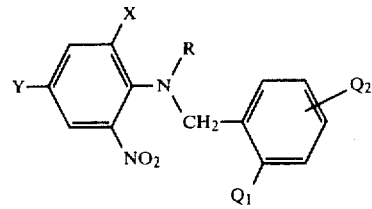

in which
  R is hydrogen, lower alkyl or allyl,
  one of X and Y is nitro and the other is trifluoromethyl,
  $Q_1$ is halogen, lower alkyl or methoxy, and
  $Q_2$ is hydrogen, halogen, lower alkyl or methoxy, are useful as herbicides and plant growth regulating agents, in particular as agents for controlling the growth of tobacco suckers. Particularly useful are those compounds in which R is ethyl, X is nitro, Y is trifluoromethyl, $Q_1$ is fluorine or chlorine, and $Q_2$ is hydrogen, methyl, fluorine or chlorine in the 6-position.

17 Claims, No Drawings

N-(ORTHO-SUBSTITUTED BENZYL)-DINITRO-TRIFLUOROMETHYL-ANILINES AS PLANT GROWTH REGULANTS

CROSS-REFERENCE TO RELATED APPLICATION

This is a continuation of application Ser. No. 628,693 filed on Nov. 5, 1975, which was a continuation-in-part of application Ser. No. 533,046 filed on Dec. 16, 1974, both now abandoned.

DETAILED DISCLOSURE

This invention concerns new N-benzyl-2-nitroaniline compounds, processes for their preparation, methods for regulating plant growth employing these compounds, and compositions containing said compounds as active substances. These compounds are useful for altering the growth pattern of growing plants, and are particularly suited for the retardation and/or control of tobacco suckers, i.e., the undesirable branching of tobacco plants.

More particularly, the invention concerns N-(ortho-substituted benzyl)-dinitro-trifluoromethyl-aniline compounds of the general formula

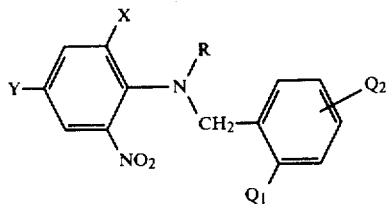

in which
R is hydrogen, lower alkyl or allyl,
one of X and Y is nitro and the other is trifluoromethyl,
$Q_1$ is halogen, lower alkyl or methoxy, and
$Q_2$ is hydrogen, halogen, lower alkyl or methoxy.

In the foregoing definition, the term "lower alkyl" indicates saturated aliphatic hydrocarbons having no more than 4 carbon atoms. Included within the definition, therefore, are methyl, ethyl, n-propyl, isopropyl, and the four butyl configurations. The term "halogen" refers to fluorine, chlorine, bromine and iodine, in particular to fluorine and chlorine.

Preferred among the compounds of formula I are those which have the structure

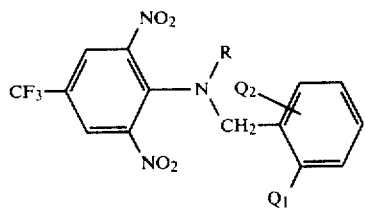

in which
R is lower alkyl,
$Q_1$ is fluorine, chlorine, methyl or methoxy, and
$Q_2$ is hydrogen, fluorine, chlorine, methyl or methoxy.

Also preferred are compounds of formula I which have the structure

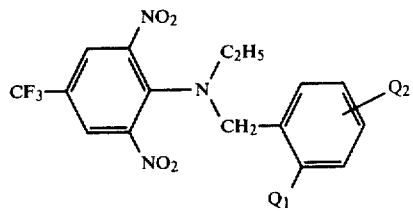

in which
$Q_1$ is methyl, fluorine or chlorine, and
$Q_2$ is hydrogen, fluorine or chlorine.

Particularly preferred are compounds of the formula

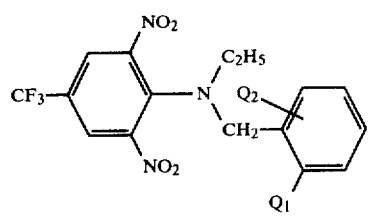

in which
$Q_1$ is fluorine or chlorine, and
$Q_2$ is methyl, fluorine or chlorine.

Especially preferred are compounds of formula IV in which each of $Q_1$ and $Q_2$ is fluorine or chlorine.

N-benzyl-dinitro-trifluoromethyl-aniline compounds are known from U.S. Pat. No. 3,686,230. The compounds of this invention, which are characterized by being substituted in the 2-position of the benzyl ring, are superior to the compounds disclosed in said patent in their use as plant-growth regulants, and as selective herbicides.

For plant growth regulating effectiveness, in particular for the control of tobacco suckers, the compounds of this invention are preferably applied at a rate of from about 10 to about 400 milligrams per plant. The compounds are most conveniently applied in the form of formulated compositions which will be discussed more fully below. When used at higher concentrations, for example, at about 0.5 to about 34 Kg. per hectare, the compounds of this invention act as herbicidal agents. When their use as herbicides is desired, they may be employed as either the sole active ingredient in herbicidal compositions, or alternatively, they may be employed in combination with one or more known herbicidal compounds.

The compounds of formula I may be prepared by reacting substantially equimolar amounts of a 2-nitro-1-chlorobenzene of formula V.

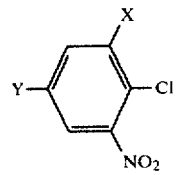

with a benzylamine of formula VI

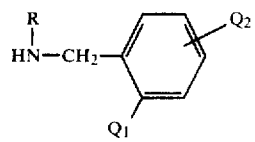

in the presence of an acid acceptor such as an alkylamine of formula VII (alkyl)$_3$N    (VII)

In these structures, X, Y, R, Q$_1$ and Q$_2$ have the meanings ascribed to them in formula (I). These reactants are dissolved in a suitable aprotic solvent, such as tetrahydrofuran, a dioxane, or low molecular weight ethers. A precipitate of trialkylamine hydrochloride appears and is filtered off. The solvent is then evaporated to yield the N-benzyl-2-nitroaniline of formula (I).

The starting materials are readily available or can be prepared by methods well-known in the art. Thus, compounds of formula (V) may be prepared by nitration of an appropriate chlorobenzene or replacement of the —OH group of a nitrophenol by a chlorine atom. Details concerning the preparation of representative examples of those compounds may be found in Bunnet et al., *J.A.C.S.* 76, 3936–39 (1954), Friederich et al. U.S. Pat. No. 2,257,093, and Soper U.S. Pat. No. 3,442,639.

The benzylamines and N-alkylbenzylamines of formula (VI) are either commercially available or may be prepared by reductive alkylation of a benzaldehyde and ammonia or an alkylamine, or conversely, reductive alkylation of a benzylamine and aliphatic aldehyde, as described by Wm. S. Emerson, *Organic Reactions* 4, 174–255 (1948).

The trialkylamine of formula (VII) functions as an acid acceptor. In lieu thereof, other compounds which will form an insoluble salt in the reaction may be used. These compounds include pyridines and alkylpyridines, alkali metal hydroxides, excess substituted benzylamine, or other acid acceptors well-known in the art. It is advantageous to use excess benzylamine as the acid acceptor, since the resulting benzylamine hydrochloride may be treated with an inorganic base, thus recovering the substituted benzylamine.

The following examples are intended to illustrate some of the embodiments of this invention. These examples are for illustrative purposes only and are not to be construed as a limitation.

EXAMPLE 1

Equimolar amounts of 4-chloro-3,5-dipitrobenzotrifluoride, N-ethyl-2-chloro-6-fluorobenzylamine, and triethylamine were dissolved separately in tetrahydrofuran. The two amines were mixed together, and added to the benzotrifluoride at a temperature below 10° C. The reaction vessel was then given a nitrogen atmosphere and capped. A precipitate of triethylamine hydrochloride appeared in a few minutes. After a few days, the precipitate was filtered off and the solvent evaporated to yield crude N-(2′-chloro-6′-fluorobenzyl)-N-ethyl-2,6-dinitro-4-trifluoromethylaniline, melting point 91°–105° C. Recrystallization from petroleum ether gives a compound with melting point 103°–104° C.

Analysis—C$_{16}$H$_{12}$ClF$_4$N$_3$O$_4$: Calc.: C, 45.57%; N, 9.96%. Found: C, 45.71%, N, 9.86%.

EXAMPLES 2–29

Additional N-benzyl-2-nitroaniline compounds are prepared by methods analogous to Example 1, as indicated in the following table, where X, Y, R, Q$_1$ and Q$_2$ are as in formula (II).

| Example | X | Y | R | Q$_1$ | Q$_2$ | Melting Point °C. |
|---|---|---|---|---|---|---|
| 2 | NO$_2$ | CF$_3$ | H | CH$_3$ | H | 133–135 |
| 3 | NO$_2$ | CF$_3$ | CH$_3$ | Cl | H | 100–102 |
| 4 | NO$_2$ | CF$_3$ | C$_2$H$_5$ | CH$_3$ | H | 103–104 |
| 5 | NO$_2$ | CF$_3$ | C$_2$H$_5$ | Cl | H | 99–101 |
| 6 | NO$_2$ | CF$_3$ | C$_2$H$_5$ | CH$_3$O | H | 93–97 |
| 7 | NO$_2$ | CF$_3$ | iC$_3$H$_7$ | F | 6-F | |
| 8 | NO$_2$ | CF$_3$ | iC$_3$H$_7$ | Cl | H | |
| 9 | NO$_2$ | CF$_3$ | allyl | Cl | 6-F | |
| 10 | NO$_2$ | CF$_3$ | CH$_3$ | Cl | 6-F | 103–104 |
| 11 | NO$_2$ | CF$_3$ | nC$_3$H$_7$ | Cl | 6-F | 109–111 |
| 12 | NO$_2$ | CF$_3$ | iC$_3$H$_7$ | Cl | 6-F | Red Oil |
| 13 | NO$_2$ | CF$_3$ | nC$_3$H$_7$ | F | H | 107–109 |
| 14 | NO$_2$ | CF$_3$ | iC$_3$H$_7$ | F | H | Red Oil |
| 15 | NO$_2$ | CF$_3$ | CH$_3$ | F | 6-F | |
| 16 | NO$_2$ | CF$_3$ | C$_2$H$_5$ | F | 6-F | |
| 17 | NO$_2$ | CF$_3$ | nC$_3$H$_7$ | F | 6-F | Red Oil |
| 18 | NO$_2$ | CF$_3$ | nC$_3$H$_7$ | Cl | 6-Cl | Red Oil |
| 19 | NO$_2$ | CF$_3$ | C$_2$H$_5$ | Cl | 6-Cl | 134–135 |
| 20 | NO$_2$ | CF$_3$ | CH$_3$ | Cl | 6-Cl | |
| 21 | NO$_2$ | CF$_3$ | iC$_3$H$_7$ | Cl | 6-Cl | |
| 22 | CF$_3$ | NO$_2$ | C$_2$H$_5$ | F | H | |
| 23 | CF$_3$ | NO$_2$ | C$_2$H$_5$ | F | 6-F | |
| 24 | CF$_3$ | NO$_2$ | C$_2$H$_5$ | Cl | 6-Cl | |
| 25 | CF$_3$ | NO$_2$ | C$_2$H$_5$ | Cl | 6-F | |
| 26 | CF$_3$ | NO$_2$ | C$_2$H$_5$ | CH$_3$O | 6-CH$_3$O | |
| 27 | CF$_3$ | NO$_2$ | C$_2$H$_5$ | CH$_3$ | 6-CH$_3$ | |
| 28 | CF$_3$ | NO$_2$ | C$_2$H$_5$ | Cl | H | |
| 29 | NO$_2$ | CF$_3$ | C$_2$H$_5$ | F | H | |

EXAMPLE 30

N-benzyl-N-ethyl-2,6-dinitro-4-trifluoromethylaniline (known from U.S. Pat. No. 3,686,280) and N-(2′-chlorobenzyl)-N-methyl-2,6-dinitro-4-trifluoromethylaniline (Example 3 herein) were applied to flats planted with ryegrass, corn, sunflower, tomato and mustard. Application was made in 25% aqueous methanol at an application rate of 5.6 Kg. per hectare. Results were measured after ten days. The flats treated with N-benzyl-N-ethyl-2,6-dinitro-4-trifluoromethylaniline showed all ryegrass killed, corn growth reduced by 50% but little effect on sunflowers, tomatoes and mustard. The flat treated with N-(2′-chlorobenzyl)-N-methyl-2,6-dinitro-4-trifluoromethylaniline showed almost complete kill of ryegrass, with little effect on the other species.

EXAMPLE 31

Plots of five Hicks tobacco plants on which suckers were beginning to appear were treated with 50 ml. of 50% aqueous acetone containing 0.1% of an octylphenoxypolyethoxyethanol (Triton X-114, sold by Rohm & Haas) and 750 ppm of certain active ingredients. Twenty-five days later, sucker size was rated. Thirty-three days later, the suckers were removed, counted and weighed. The results, for various active ingredients are shown in the following table:

| Active Ingredient | Sucker Size | No. of Suckers on 5 Plants | Sucker Weights (gms) |
|---|---|---|---|
| N-(2′-chloro-6′-fluoro-benzyl)-N-ethyl-2,6- | | | |

| Active Ingredient | Sucker Size | No. of Suckers on 5 Plants | Sucker Weights (gms) |
|---|---|---|---|
| dinitro-4-trifluoro-Methylaniline (according to this invention) | 1.0 | 0 | 0 |
| N-sec.butyl-4-ter.butyl-2,6-dinitroaniline (known compound) | 1.0 | 2 | 14 |
| Maleic hydrazine | 2.2 | 17 | 41 |
| Check (untreated) | 4.0 | 14 | 820 |

The rating for sucker size represents the average of 5 plants. A rating of 1 indicates the size of from 0 to 2.5 cm. A rating of 2 indicates the size of from 2.5 to 5.1 cm. A rating of 3 indicates the size of from 5.1 to 10.2 cm. A rating of 4 indicates the size of more than 10.2 cm.

The production of herbicidal compositions according to the invention is carried out in a manner well-known in the art by the intimate mixing and grinding of the active substances of the general formula I with suitable carriers, optionally with the addition of dispersing agents or solvents which are inert to the active substances. The active substances can exist and be used in the following forms:

as solids: dusts, sprinkling agents, granulates, coated granules, impregnated granules and homogeneous granules;

as concentrates of active substances dispersible in water: wettable powder, pastes, emulsions;

as liquids: solutions, aerosols.

To produce the solid forms (dusts, sprinkling agents, granulates), the active substances are mixed with solid carriers. Suitable carriers are, e.g., kaolin, talcum, bole, chalk, limestone, ground limestone, dolomite, diatomaceous earth, precipitated silicic acid, alkaline earth silicates, sodium and potassium aluminum silicates (feldspar and mica), calcium and magnesium sulfates, magnesium oxide, ground synthetic plastics, fertilizers such as ammonium sulfate, ammonium phosphate, ammonium nitrate, ureas, ground vegetable products such as grain flour, bark flour, sawdust, ground nut shells, cellulose powder, residues of plant extractions, activated charcoal, etc. These carriers can be used separately or they can be mixed with each other.

The grain size of the carriers is, for dusts, advantageously up to ca. 0.1 mm, for sprinkling agents it is ca. 0.075 to 0.2 mm and for granulates 0.2 mm upwards.

The concentrations of active substances in the solid preparations are, as a rule, 0.5 to 80% of the total weight.

To these mixtures can also be added additives which stabilize the active substance and/or non-ionic, anion-active and cation-active substances, which, for example, improve the adhesion of the active substances on plants and parts of plants (glues and adhesives) and/or ensure a better wettability (wetting agents) and also dispersibility (dispersing agents). The following are examples of adhesives: olein-chalk mixtures, cellulose derivatives (methyl cellulose, carboxymethyl cellulose), hydroxyethyl glycol ethers of mono- and di-alkyl phenols having 5 to 15 ethylene oxide radicals per molecule and 8 or 9 carbon atoms in the alkyl radical, lignin sulfonic acids, their alkali and alkaline earth metal salts, polyethylene glycol ethers, fatty alcohol polyethylene glycol ethers having 5 to 20 ethylene oxide radicals per molecule and 8 to 18 carbon atoms in the fatty alcohol part, condensation products of ethylene oxide, propylene oxide, polyvinyl pyrrolidones, polyvinyl alcohols, condensation products of urea/formaldehyde as well as latex products.

Concentrates of active substances which can be dispersed in water (wettable powders), pastes and emulsion concentrates, are agents which can be diluted with water to give any desired concentration. They consist of active substances, carriers, optionally additives which stabilize the active substance, surface agent substances and anti-foaming agents and, optionally, solvents. The concentration of active substance in these agents is 5 to 80% of the total weight of the latter.

The wettable powders and pastes are obtained by mixing and grinding the active substances with dispersing agents and pulverulent carriers in suitable devices until homogeneity is attained. Suitable carriers are, for example, those previously mentioned for solid preparations. It is advantageous in some cases to use mixtures of different carriers. Suitable dispersing agents are, e.g., condensation products of sulfonated naphthalene and sulfonated naphthalene derivatives with formaldehyde, condensation products of naphthalene or of naphthalene sulfonic acids with phenol and formaldehyde, also alkali, ammonium and alkaline earth metal salts of lignin sulfonic acid, also alkylaryl sulfonates, alkali and alkaline earth metal salts of dibutyl naphthalene sulfonic acid, fatty alcohol sulfates such as salts of sulfated fatty alcohol glycol ethers, the sodium salt of oleyl ethionate, the sodium salt of oleyl methyl tauride, ditertiary acetylene glycols, dialkyldilauryl ammonium chloride and fatty acid alkali and alkaline earth metal salts.

Examples of anti foaming agents are: silicones, etc. The active substances are so mixed, ground, sieved and strained with the above-mentioned additives that the solid particle size in wettable powders does not exceed 0.02-0.04 mm and, in the case of pastes, 0.003 mm. To produce emulsion concentrates and pastes, dispersing agents such as those stated in the previous sections, organic solvents and water are used. Examples of solvents are: alcohols, benzene, xylenes, toluene, dimethyl sulfoxide and mineral oil fractions boiling between 120° and 350° C. The solvents must be practically without smell, not phytotoxic, inert to the active substances and not easily flammable.

In addition, the agents according to the invention can be used in the form of solutions. For this application, the active substance or substances of the general formula I are dissolved in suitable organic solvents, mixtures of solvets or in water. Aliphatic and aromatic hydrocarbons, chlorinated derivatives thereof, alkyl naphthalenes, mineral oils, on their own or mixed with each other, can be used as organic solvents. The solvents should contain the active substances within a concentration range of 1 to 20% calculated on the total weight of the resulting solution.

Other biocidal active substances or agents can be mixed with the described compositions according to the invention. Thus, in addition to the stated compounds of the general formula I and other herbicides, the new agents can also contain, e.g., insecticides, fungicides, bactericides, fungistatics, bacteriostatics or nematocides in order to widen the range of action. The compositions according to the invention can also contain fertilizers and micronutrients.

I claim:

1. A compound of the formula

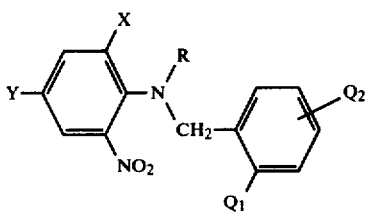

in which
R is hydrogen, lower alkyl or allyl,
one of X and Y is nitro and the other is trifluoromethyl,
$Q_1$ is halogen, lower alkyl or methoxy, and
$Q_2$ is hydrogen, halogen, lower alkyl or methoxy.

2. A compound according to claim 1 in which X is nitro; Y is trifluoromethyl; R is lower alkyl; $Q_1$ is fluorine, chlorine, methyl or methoxy; and $Q_2$ is hydrogen, fluorine, chlorine, methyl or methoxy in the 6-position.

3. A compound according to claim 2 in which R is ethyl; $Q_1$ is methyl, fluorine or chlorine; and $Q_2$ is hydrogen, methyl, fluorine or chlorine.

4. A compound according to claim 3 in which each of $Q_1$ and $Q_2$ is fluorine or chlorine.

5. The compound of claim 4 which is N-(2'-chloro-6'-fluorobenzyl)-N-ethyl-2,6-dinitro-4-trifluoromethylaniline.

6. The compound of claim 3 which is N-(2'-chlorobenzyl)-N-ethyl-2,6-dinitro-4-trifluoromethylaniline.

7. The compound of claim 4 which is N-(2',6'-difluorobenzyl)-N-ethyl-2,6-dinitro-4-trifluoromethylaniline.

8. The compound of claim 4 which is N-(2',6'-dichlorobenzyl)-N-ethyl-2,6-dinitro-4-trifluoromethylaniline.

9. The compound of claim 3 which is N-(2'-fluorobenzyl)-N-ethyl-2,6-dinitro-4-trifluoromethylaniline.

10. The compound of claim 2 which is N-(2'-chlorobenzyl)-N-methyl-2,6-dinitro-4-trifluoromethylaniline.

11. A composition for regulating the growth of plants which comprises (1) as active ingredient a compound of the formula

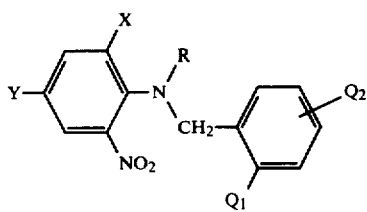

in which
R is hydrogen, lower alkyl or allyl,
one of X and Y is nitro and the other is trifluoromethyl,
$Q_1$ is halogen, lower alkyl or methoxy, and
$Q_2$ is hydrogen, halogen, lower alkyl or methoxy and
(2) a carrier.

12. A composition according to claim 11 in which X is nitro; Y is trifluoromethyl; R is lower alkyl: $Q_1$ is fluorine, chlorine, methyl or methoxy; and $Q_2$ is hydrogen, fluorine, chlorine, methyl or methoxy in the 6-position.

13. A method for regulating the growth of plants which comprises applying thereto an effective amount of a compound of the formula

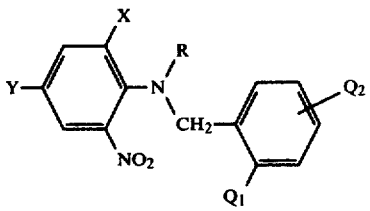

in which
R is hydrogen, lower alkyl or allyl,
one of X and Y is nitro and the other is trifluoromethyl,
$Q_1$ is halogen, lower alkyl or methoxy, and
$Q_2$ is hydrogen, halogen, lower alkyl or methoxy.

14. A method according to claim 13 in which X is nitro; Y is trifluoromethyl; R is lower alkyl; $Q_1$ is fluorine, chlorine, methyl or methoxy; and $Q_2$ is hydrogen, fluorine, chlorine, methyl or methoxy in the 6-position.

15. A method for controlling undesirable axillary branching of tobacco plants which comprises applying to said plants an effective amount of a compound of the formula

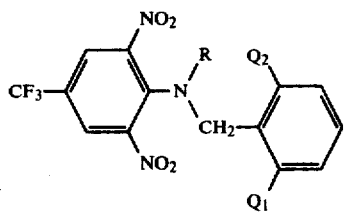

in which
R is lower alkyl, and
$Q_1$ is fluorine, chlorine, methyl or methoxy, and
$Q_2$ is hydrogen, fluorine, chlorine, methyl or methoxy.

16. A method according to claim 15 in which R is ethyl; $Q_1$ is fluorine, chlorine or methyl; and $Q_2$ is hydrogen, fluorine, chlorine or methyl.

17. The method of claim 16 in which the compound is N-(2'-chloro-6'-fluorobenzyl)-N-ethyl-2,6-dinitro-4-trifluoromethylaniline.

* * * * *